US009993553B2

United States Patent
Guo et al.

(10) Patent No.: US 9,993,553 B2
(45) Date of Patent: Jun. 12, 2018

(54) METHODS AND COMPOSITIONS FOR TARGETED RELEASE OF MOLECULES FROM NANOSCALE CARRIERS

(71) Applicant: The Regents of the University of California, Oakland, CA (US)

(72) Inventors: Ting Guo, Davis, CA (US); Zane B. Starkewolfe, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 303 days.

(21) Appl. No.: 14/213,148

(22) Filed: Mar. 14, 2014

(65) Prior Publication Data

US 2014/0273215 A1    Sep. 18, 2014

Related U.S. Application Data

(60) Provisional application No. 61/785,526, filed on Mar. 14, 2013.

(51) Int. Cl.
| | |
|---|---|
| C12N 5/09 | (2010.01) |
| A61K 41/00 | (2006.01) |
| A61K 47/69 | (2017.01) |
| B82Y 5/00 | (2011.01) |

(52) U.S. Cl.
CPC ...... *A61K 41/0042* (2013.01); *A61K 47/6923* (2017.08); *B82Y 5/00* (2013.01)

(58) Field of Classification Search
None
See application file for complete search history.

(56) References Cited

U.S. PATENT DOCUMENTS

| | | | |
|---|---|---|---|
| 6,989,153 | B2 | 1/2006 | O'Brien et al. |
| 8,535,712 | B2 | 9/2013 | O'Brien et al. |

OTHER PUBLICATIONS

Qi et all. 2008. Emerging application of quantum dots for drug delivery and therapy. Expert Opinion Drug Delivery vol. 5, No. 3, pp. 263-267.*
Park 2012. Preparation of concentrated colloids of gold core-silica shell nanoparticles for biomedical applications. Methods in Molecular Biology, 906, pp. 21-31. doi: 10.1007/978-1-61779-953-2_2.*
Gao et al. 2004. In vivo cancer targeting and imaging with semiconductor quantum Dots. Nature Biotechnology, vol. 22, pp. 969-976.*
Foley et al.. Enhanced relaxation of nanoparticle-bound supercoiled DNA in X-ray Radiation. Chemical. CommunicationThis journal is _ The Royal Society of Chemistry 2005, pp. 3192-3194.*
Shi et al. 2007. Tailored Core-Shell-Shell Nanostructures: Sandwiching Gold Nanoparticles between Silica Cores and Tunable Silica Shells. Langmuir, vol. 23, pp. 9455-9462.*

Ahn, G-O., Optimization of the Auxillary Ligand Shell of Cobalt(III)(8-hydroxyquinoline) Complexes as Model Hypoxia-Selective Radiation-Activated Prodrugs; Radiation Research 162 (2004) 315-325.
Bontenbal, Marijke et al.; Uptake and distribution of doxorubicin in hormone-manipulated human breast cancer cell in vitro. Breast Cancer Research and Treatment 51 (1998) 139-148.
Carter, Joshua D., et al.; Enhanced single strand breaks of supercolied DNA in a matrix of gold nanotubes under X-ray irradiation; Journal of Colloid and Interface Science 378 (2012) 70-76.
Carter, Joshua D., et al.; Nanoscale Energy Deposition by X-ray Absorbing Nanostructures; Journal of Physical Chemistry B, 111 (2007) 11622-11625.
Cheng, Neal N., et al.; Chemical Enhancement by Nanomaterials under X-ray Irradiation; Journal of the American Chemical Society 134 (2012) 1950-1953.
Dhar, Shanta, et al.; Polyvalent Oligonucleotide Gold Nanoparticle Conjugates as Delivery Vehicles for Platinum(IV) Warheads; Journal of the American Chemical Society 131 (2009) 14652-14653.
Di Marco. A., et al.; Adriamycin (NSC-123,127): A New Antibiotic with Antitumor Activity; Cancer Chemotherapy Reports 53 (1969) 33-37.
Fisher, Bernard. et al.; Five-Year Results of a Randomized Clinical Trial Comparing Toal Mastectomy and Segmental Mastectomy With or Without Radiation in the Treatment of Breast Cancer; New England Journal of Medicine 312 (1985) 665-673.
Foley, Erika A., et al.; Enhanced retaxation of nanoparticle-bound supercoiled DNA in X-ray radiation; Chem. Commun., (2005) 3192-3194.
Fornari, Frank A., et al.; Interference by Doxorubicin with DNA Unwinding in MCF-7 Breast Tumor Cells; Molecular Pharmacology 45 (1993) 649-656.
Franken, Nicolaas A.P., et al.; Clonogenic assay of cells in vitro; Nature Protocols. 1 (2006) 2315-2319.
Giljohann, David A., et al.; Oligonucleotide Loading Determines Cellular Uptake of DNA-Modified Gold Nanoparticles; Nano Letters 7 (2007) 3818-3821.
Gobin, Andre, et al.; Near-Infrared Resonant Nanoshells for Combined Optical Imaging and Photothermal Cancer Therapy; Nano Letters 7 (2007) 1929-1934.
Hu, Shang-Hsiu, et al.; Remotely nano-rupturable yolk/shell capsules for magnetically-triggered drug release; Chem. Commun., 47 (2011) 1776-1778.
Li, Weiyang, et al.; Gold Nanocages Covered with Thermally-responsive Polymers for Controlled Release by High-intensity Focused Ultrasound; Nanoscale 3(4) (2011) 1724-1730.
Martucci, F., et al.; Hypofractionated Image Guided 4D Radiotherapy (4D-IGRT) in Limited Non Small Cell Lung Cancer; (Abstract-Strahlenther Onkol); Radiation Oncology (2011) 187:529.

(Continued)

Primary Examiner — Louise W Humphrey
Assistant Examiner — Kailash C Srivastava
(74) Attorney, Agent, or Firm — Kilpatrick Townsend & Stockton LLP (57) ABSTRACT

The present disclosure relates generally to the field of nanoscale materials, and more specifically to the field of nanoscale materials for activating delivered molecules at a target location.

33 Claims, 5 Drawing Sheets

(56) References Cited

OTHER PUBLICATIONS

Nguyen, Thao M., et al.; Template-synthesized multifunctional nanotube for targeting, imaging, and triggered drug releasing; (Abstract) COLL 226 (2009).

Qin, Guotlng, et al.; Partially polymerized liposomes: stable against leakage yet capable of instantaneous release for remote controlled drug delivery; Nanotechnology 22 (2011) 1-14.

Scaffidi, Jonathan P., et al.; Activity of Psoralen-Functionalized Nanoscintillators against Cancer Cells upon X-ray Excitation; ACS NANO 5 (2011)4679-4687.

Schroeder, Avi. et al.; Ultrasound, liposomes, and drug delivery: principles for using ultrasound to control the release of drugs from liposomes; Chemistry and Physics of Lipids 162 (2009) 1-16.

Senthi, Sashendra. et al.; Patterns of disease recurrence after stereotactic ablative radiotherapy for early stage non-small cell lung cancer: a retrospective analysis; Lancet Oncol 13 (2012) 802-809.

Tanabe, Kazuhito, et al.; Reductive activation of 5-fluorodeoxyuridine prodrug possessing azide methyl group by hypoxic X-irradiation; Bioorganic & Medicinal Chemistry Letters 22 (2012) 1682-1685.

Turkevich, John, et al.; A Study of the Nucleation and Growth Processes in the Synthesis of Colloidal Gold; P.S. Williams—Discussions of the Faraday Society (1951) 55-75.

Von Hoff, Daniel D., et al.; Risk Factors for Doxorubicin-Induced Congestive Heart Failure; Annals of Internal Medicine 91 (1979) 710-717.

Wang, Feng. et al.; Doxorubicin-Tethered Responsive Gold Nanoparticles Facilitate Intracellular Drug Delivery for Overcoming Multidrug Resistance in Cancer Cells; ACS NANO 5 (2011) 3679-3692.

* cited by examiner

METHODS AND COMPOSITIONS FOR TARGETED RELEASE OF MOLECULES FROM NANOSCALE CARRIERS

CROSS-REFERENCE TO RELATED APPLICATION(S)

This application claims the benefit of U.S. Provisional Application No. 61/785,526 filed Mar. 14, 2013, which is incorporated herein by reference in its entirety.

STATEMENT REGARDING FEDERALLY-SPONSORED RESEARCH

This invention was made with government support under Contract No. W81XWH-10-1-1031 awarded by The United States Army. The government has certain rights in the invention.

FIELD

The present disclosure relates generally to the field of nanoscale materials, and more specifically to the field of nanoscale materials for activating delivered molecules at a target location.

BACKGROUND

Small molecule chemotherapeutic drugs such as doxorubicin (DOX) have been employed in cancer therapy (Dimarco et al., 1969). However, their effectiveness is hampered by specific and systemic toxicity (Vonhoff et al., 1979). With limited success, prodrugs have been shown to help reduce systemic toxicity (Rooseboom et al., 2004). To increase efficacy and overcome the problem of systemic toxicity, drug carriers or vehicles, including nanomaterials, have been developed to deliver drug molecules to tumors (Gabizon et al., 1994; Arora et al., 2012; Qin et al., 2011). Drugs delivered in these carriers must be released upon reaching tumor sites, either through internal/natural or external triggering mechanisms. Natural triggering has the advantage of using the tumor itself to trigger the release (Dhar et al., 2009). External triggering such as microwaves, ultrasound, light and especially near IR light, and magnetic fields have been explored as the trigger for the release of drug molecules (Schroeder et al., 2009; West et al., 2007; Liu et al., 2011; Wang et al, 2011).

X-rays can potentially become a successful external triggering tool to release drugs from nanomaterial or nanoparticle drug carriers (NDC). Because X-rays are highly penetrating and have been used clinically in diagnosis and treatment of tumor, X-ray triggered release mechanisms may find immediate clinical applications. Demonstrations of X-ray triggered, controlled release of drugs from carriers or vehicles in pure water have been reported (O'Brien et al., 2001). However, no release has been shown in vitro or in vivo, such as in living cells, which are nearly hundred times more radiation resistant due to the presence of radical scavengers. Other triggering modalities such as infrared light and microwave have been used with other types of nanomaterial-based drug delivery vehicles. However, they all suffer certain shortcomings such as lack of location precision or shallow penetration depths. Prodrugs have been developed in the past, in which the drug portion can be cleaved from the base molecules upon X-ray irradiation. However, these prodrugs still retain systematic toxicity because they tend to be deposited in many places unintended for delivery.

Thus, there exists a need for a drug delivery device that can deliver a prodrug to a target cellular location and controllably release the drug at that target cellular location.

BRIEF SUMMARY

In certain aspects, the present disclosure relates to a nanoparticle-based method of providing a treatment to a target cell, the method comprising: a) contacting the target cell with a nanomaterial composition, the nanomaterial composition comprising a nanoparticle linked, via a linker, to a therapeutic molecule, and b) cleaving the link between the nanoparticle and the therapeutic molecule with irradiation energy to produce a liberated therapeutic molecule, wherein the biological activity of the liberated therapeutic molecule is greater than the biological activity of the nanomaterial composition. In some embodiments, the nanomaterial composition further comprises a drug base scaffold wherein the drug base scaffold is attached to the linker and the drug base scaffold is attached to a therapeutic molecule. In some embodiments, the drug base scaffold is a DNA molecule. In some embodiments, the nanoparticle comprises a core comprising a metal. In some embodiments, the metal is Au. In some embodiments, the nanoparticle comprises a shell comprising silica. In some embodiments, the shell has attached, at its surface, PEG ligands. In some embodiments, the shell has attached, at its surface, targeting moieties. In some embodiments, the linker is a DNA molecule. In some embodiments, the therapeutic molecule is doxorubicin. In some embodiments, the irradiation energy is X-rays. In some embodiments, the target cell is a cancer cell.

In some aspects, the present disclosure further relates to a nanoparticle-based method of providing a treatment to a living system, the method comprising: a) administering to the living system a nanomaterial composition, the nanomaterial composition comprising a nanoparticle linked, via a linker, to a therapeutic molecule, and b) irradiating the living system with irradiation energy sufficient to cleave the link between the nanoparticle and the therapeutic molecule to produce a liberated therapeutic molecule, wherein the biological activity of the liberated therapeutic molecule is greater than the biological activity of the nanomaterial composition. In some embodiments, the nanomaterial composition further comprises a drug base scaffold wherein the drug base scaffold is attached to the linker and the drug base scaffold is attached to a therapeutic molecule. In some embodiments, the drug base scaffold is a DNA molecule. In some embodiments, the nanoparticle comprises a core comprising a metal. In some embodiments, the metal is Au. In some embodiments, the nanoparticle comprises a shell comprising silica. In some embodiments, the shell has attached, at its surface, PEG ligands. In some embodiments, the shell has attached, at its surface, targeting moieties. In some embodiments, the linker is a DNA molecule. In some embodiments, the therapeutic molecule is doxorubicin. In some embodiments, the irradiation energy is X-rays. In some embodiments, the target cell is a cancer cell.

In another aspect, the present disclosure further relates to a nanomaterial composition comprising a nanoparticle linked, via a linker, to a therapeutic molecule. In some embodiments, the composition further comprises a drug base scaffold wherein the drug base scaffold is attached to the linker and the drug base scaffold is attached to a therapeutic molecule. In some embodiments, the drug base scaffold is a DNA molecule. In some embodiments, the nanoparticle comprises a core comprising a metal. In some embodiments, the metal is Au. In some embodiments, the nanoparticle comprises a shell comprising silica. In some embodiments, the shell has attached, at its surface, PEG ligands. In some embodiments, the shell has attached, at its surface, targeting moieties. In some embodiments, the linker is a DNA molecule. In some embodiments, the therapeutic molecule is doxorubicin.

DETAILED DESCRIPTION

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

The present disclosure relates generally to nanoscale materials, and more specifically to the use of nanoscale materials for activating delivered molecules at a target location.

The present disclosure is based, at least in part, on the development of nanoparticle drug carriers (NDCs) that can deliver large quantities of drugs to tumor cells. Once the drugs in these secured nanoparticle drug carriers are delivered into the tumor cells, X-rays emitted from a conventional X-ray tube operated at 130 keV were shown to trigger to release of the drugs by cleaving the chemical bonds of the molecules linking the drug molecules to the nanoparticle drug carriers. Applicants demonstrated that gold (Au) nanoparticles can be used as the base of nanoparticle drug carriers, which are linked to the drug doxorubicin via a DNA linker. The cleaved doxorubicin from delivered nanoparticle drug carriers into breast cancer cells activated with this X-ray source was adequate to reduce cell proliferation by 3% per Gy of X-ray radiation. The activated delivery method using X-ray activated nanoparticle drug carriers allows for activation of the delivered inactive molecules at a target location. Applicant's design of nanoparticle drug carriers allows for loading of many drug molecules per carrier. Even if only a small percentage of the drug molecules were released from irradiation activation, the amount released were sufficient to significantly affect the breast cancer cells.

Nanomaterial Compositions

Figure 4:
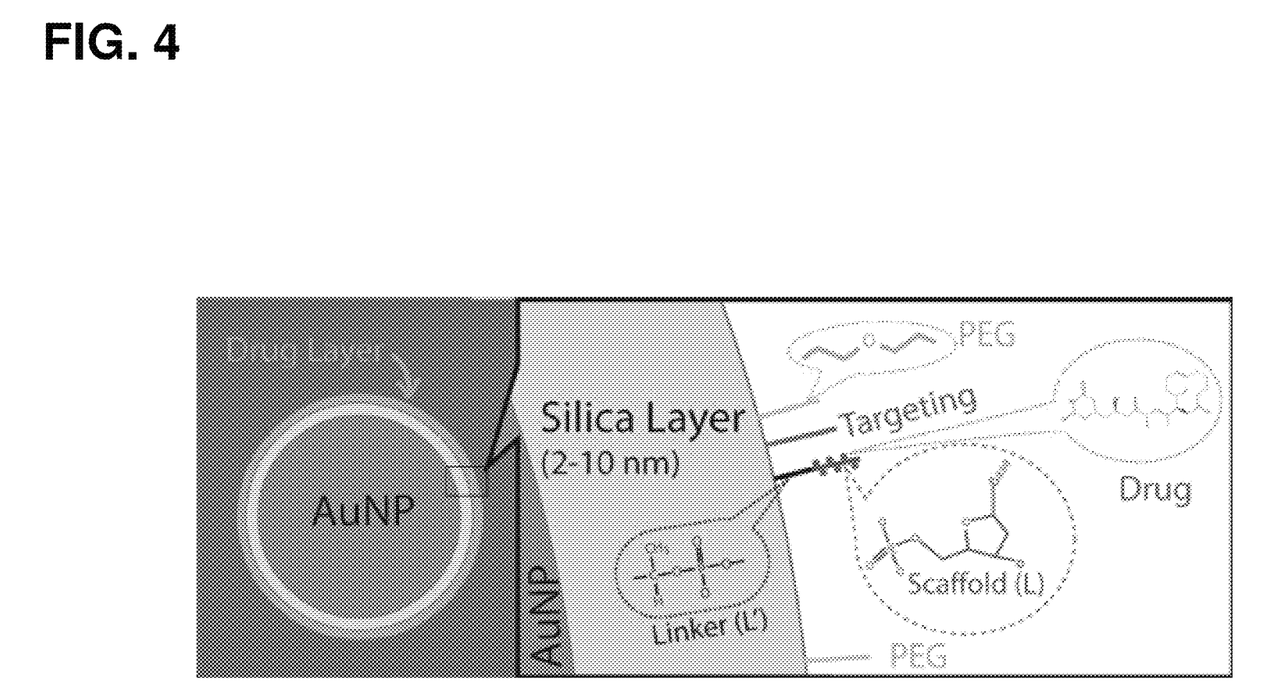
FIG. 4 illustrates an exemplary embodiment of an X-ray activated nanoparticle drug carrier (NDC).

FIG. 4 illustrates an exemplary embodiment of a nanomaterial composition of the present disclosure. The nanomaterial composition contains a metal-based nanoparticle, a linker, and a therapeutic molecule. The nanomaterial also contains a drug base scaffold where the drug base scaffold is attached to the linker and the drug base scaffold is attached to a therapeutic molecule. "Linked," as used herein, differs from "attached" in that two entities that are linked may not necessarily be directly attached, but are nevertheless indirectly connected. Note that the various features of the nanomaterial composition may vary and additional embodiments are discussed herein. The exemplary nanomaterial composition illustrated in FIG. 4 may be referred to as a nanoparticle drug carrier (NDC).

Nanoparticles

The nanomaterial compositions of the present disclosure contain a nanoparticle. The nanoparticle may be a metal-based nanoparticle where the nanoparticle is composed, at least in part, of a metal. The nanoparticle forms the base of the nanomaterial composition and is linked to a therapeutic molecule in the nanomaterial composition. As shown in the exemplary embodiment in FIG. 4, the metal-based nanoparticle is a gold (Au) nanoparticle, or AuNP, that forms the base of the nanoparticle drug carrier and is linked, via a linker, to a therapeutic molecule in the nanoparticle drug carrier.

The nanoparticle may contain a core and a shell. As shown in the exemplary embodiment in FIG. 4, the core is a gold nanoparticle and the shell is a silica ($SiO_2$ or silicon dioxide) layer. The thickness of the shell may be from about 2 nm to about 10 nm. Note that other dimensions are also possible, including values lower than 2 nm and values higher than 10 nm.

Various nanoparticles are known in the art and may serve as the base of the nanomaterial compositions described herein. For example, these nanoparticles may include silica nanoparticles, silica-coated gold nanoparticles, silica-coated silver nanoparticles, tungsten oxide nanoparticles, titanium nanoparticles, rare earth nanoparticles such as cerium oxide nanoparticles, and other biocompatible nanoparticles such as dendrimers and polymers. Further, nanoparticles may be composed of an organic material, an inorganic material, or a combination of an organic material and an inorganic material.

The size of the nanoparticle may range from 1 nm to 300 nm. Note that the dimensions of the nanoparticle may vary and other dimensions may be used in the nanoparticles described herein, including nanoparticles with dimensions less than 1 nm and nanoparticles with dimensions greater than 300 nm. The nanoparticles may have a dimension of about 15 nm. The nanoparticles may have a dimension of about 50 nm. The nanoparticles may have a dimension of about 100 nm.

Linkers

The nanomaterial compositions of the present disclosure contain a linker. The linker is the molecular unit that may be cleaved to produce a liberated therapeutic compound. The linker is directly attached, at one end, to either the core or the shell of the nanoparticle in a nanomaterial composition. The linker may be linked to a therapeutic molecule. As shown in the exemplary embodiment in FIG. 4, the linker is directly attached, at one end, to the silica shell of a gold nanoparticle and is further linked to one or more therapeutic molecules in the nanoparticle drug carrier via a drug base scaffold. The linker may also serve as the drug base scaffold and be directly attached to a therapeutic molecule. Drug base scaffolds of the present disclosure are further discussed herein.

Various linkers are known in the art and may serve as the molecular unit that may be cleaved to produce a liberated therapeutic compound. The linkers may be, for example, naturally occurring DNA molecules, oligosaccharides, specially engineered DNA molecules, and other polyester phosphate based molecules to which one or more therapeutic molecules can be attached. The linkers may also be, for example, disulfide, diselenide and other chemical bonds. Linkers containing multiple such bonds may be synthesized for this purpose. Various linkers may be used in the nanomaterial compositions of the present disclosure as long as the chemical bonds forming the linker are susceptible to cleavage by electrons directly or reactive oxygen species.

The number of linkers attached to a single nanoparticle may range from one to many thousands. The linkers may also cover, for example, a fraction of the surface area of the nanoparticle or a substantial portion of the surface area of the nanoparticle. The number of linkers linked to a nanoparticle may vary.

Drug Base Scaffolds

The nanomaterial compositions of the present disclosure contain a drug base scaffold. The drug base scaffold is the molecular unit that serves as the base of attachment for a therapeutic molecule in a nanomaterial composition. Thus, therapeutic molecules of the present disclosure are directly attached to a drug base scaffold. The linker in a nanomaterial composition may also serve as the drug base scaffold in the nanomaterial composition. In this embodiment, the linker, which is also the drug base scaffold, is directly attached to a therapeutic molecule while also being directly attached to a nanoparticle. The linker and the drug base scaffold in a nanomaterial composition may also be independent entities. In this embodiment, the linker is attached, at one end, to a nanoparticle and further directly attached at the opposite end, or the end not attached to the nanoparticle, to the drug base scaffold which is directly attached to a therapeutic molecule. As shown in the exemplary embodiment in FIG. 4, the linker is attached, at one end, to the silica shell of a gold nanoparticle and is further directly attached, at the end not attached to the gold nanoparticle, to a drug base scaffold, which is directly attached to one or more therapeutic molecules in the nanoparticle drug carrier.

Various drug base scaffolds are known in the art and may serve as the base of attachment for a therapeutic molecule in a nanomaterial composition of the present disclosure. The drug base scaffolds may be, for example, DNA strands, hyaluronic acid (hyaluronan), peptides, and polyester phosphate molecules. Various drug base scaffolds may be used herein as long as the drug base scaffold has a region that is capable of having a therapeutic molecule directly attached.

A molecule in a nanomaterial composition of the present disclosure may serve as both the linker and the drug base scaffold. For example, a DNA molecule can be the drug base scaffold to which a therapeutic molecule is attached, while also serving as the linker and thus being directly attached to a nanoparticle. The linker and the drug base scaffold may also be, for example, independent entities. For example, the drug base scaffold may be a DNA molecule that is attached to a therapeutic molecule. This DNA molecule, serving as the drug base scaffold is then directly attached to the linker molecule, which may be, for example, another DNA strand or other suitable linker. Although the linker and the drug base scaffold may be independent entities, they may be similar or identical molecules. For example, the linker and the drug base scaffold may be DNA molecules. The linker and the drug base scaffold may also be independent entities and different molecules. One of skill in the art would readily recognize suitable linkers and drug base scaffolds, as well as various ways to link a therapeutic molecule to a nanoparticle, that are suitable for use in the nanomaterial compositions described herein.

Therapeutic Molecules

The nanomaterial compositions of the present disclosure contain a therapeutic molecule. The therapeutic molecule is attached to a drug base scaffold, the drug base scaffold being attached, directly or indirectly, to a nanoparticle in the nanomaterial composition. As shown in the exemplary embodiment in FIG. 4, the drug base scaffold is attached to multiple therapeutic molecules, which, in the exemplary embodiments, are drug molecules. In this exemplary embodiment, the drug molecule is doxorubicin. The doxorubicin molecules are directly attached to the drug base scaffold, which is directly attached to the linker, which is directly attached to the gold nanoparticle in the nanoparticle drug carrier. Cleavage of the link between a nanoparticle and a therapeutic molecule produces a liberated therapeutic molecule Liberated therapeutic molecules of the present disclosure have biological activity. Various molecules having biological activity are known in the art and may include, for example, molecules that have anti-cancer activity. Various therapeutic molecules may find use in the nanomaterial compositions of the present disclosure such as, for example, doxorubicin. The therapeutic molecules may be, for example, regular cancer drugs or natural products that are more or less toxic than doxorubicin. Exemplary cancer drug molecules may include, for example, Fluorouracil, Paclitaxel, and Zevalin, which are among the available cancer drugs. Exemplary natural products may include, for example, Fredericamycin, C-1027, and Leinamycin. Other therapeutic molecules may include, for example, proteins, proteases, DNA nucleases, enzymes, small RNAs (sRNA), and other biological molecules.

As stated above, the nanomaterial compositions of the present disclosure contain a therapeutic molecule. Therapeutic molecules of the present disclosure are attached to a drug base scaffold. The drug base scaffold may also serve as the linker. A single drug base scaffold in a nanomaterial composition may have attached, for example, one therapeutic molecule. A single drug base scaffold may have attached, for example, one or more therapeutic molecules. A single drug base scaffold may have attached, for example, two, three, four, five, six, seven, eight, nine, ten, eleven, or twelve or more therapeutic molecules. Note that the number of therapeutic molecules attached to a single drug base scaffold may vary and may include, for example, more than twelve therapeutic molecules. The number of therapeutic molecules capable of being attached to a single drug base scaffold may depend upon, for example, the length of the molecule serving as the drug base scaffold, the molecular architecture of this molecule, and the size and type of therapeutic molecule being attached to the drug base scaffold.

Additional Features

Nanomaterial compositions of the present disclosure may contain or exhibit additional features that aid in their use in providing a molecule to a target cell.

Other agents may be linked to the surface of gold nanoparticles, which may include, for example, tumor cell targeting agents such as antibodies, peptides, and proteins that can target cancer cells and increase uptake by tumor. Folic acid may be coated on the surface of the nanoparticles to increase their uptake into cancer cells. PEG ligands may be added to the surface of nanoparticles to increase solubility. One of skill in the art would recognize additional agents that may be used in the nanomaterial compositions of the present disclosure.

Figure 5:
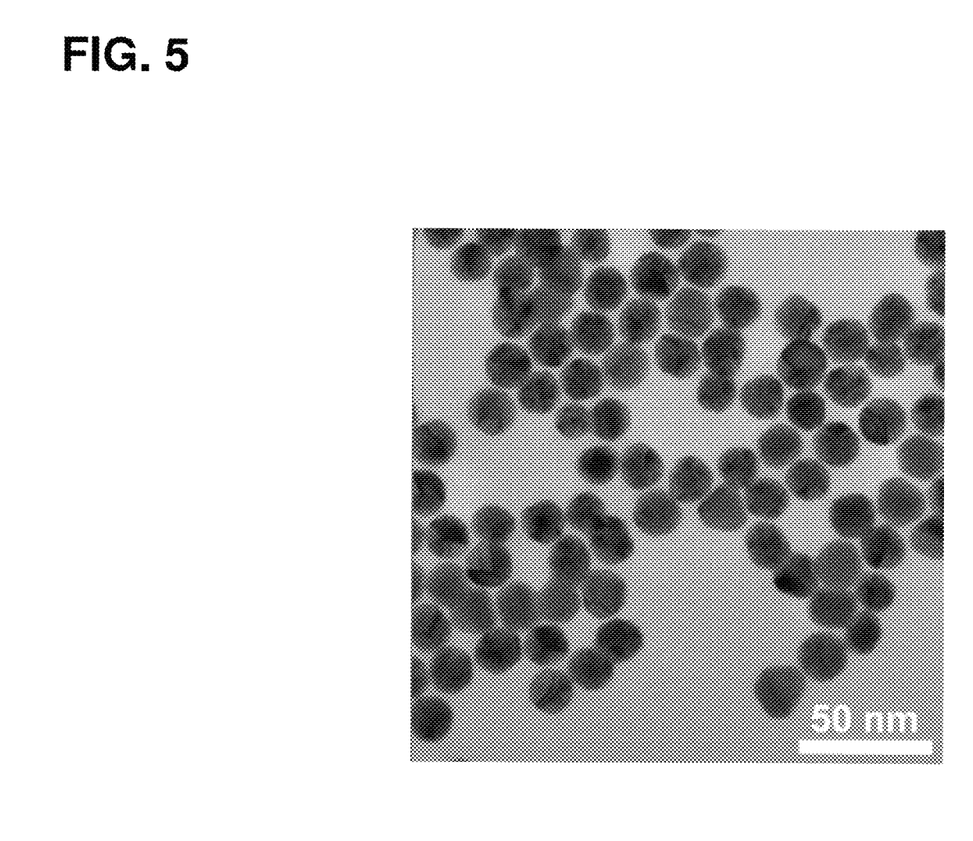
FIG. 5 illustrates an actual depiction of synthesized nanoparticle drug carriers (NDCs). NDCs were imaged using transmission electron microscopy (TEM). Length of the white scale bar denotes a length of 50 nanometers (nm).

FIG. 5 illustrates an actual depiction of a nanomaterial composition. In this depiction, the nanomaterial composition is a nanoparticle drug carrier (NDC), with each spherical object depicted being an independent NDC. The NDC is a gold nanoparticle (AuNP) attached to a DNA linker molecule. The DNA linker molecule also serves as the drug base scaffold and up to nine doxorubicin drug molecules are attached to each DNA linker attached to a gold nanoparticle. The average size of each NDC is 15.9 nm±1.2 nm.

Methods of Treatment

The present disclosure provides nanoparticle-based methods of providing a treatment to a target cell involving: a) contacting the target cell with a nanomaterial composition including a nanoparticle linked, via a linker, to a therapeutic molecule, and b) cleaving the link between the nanoparticle and the therapeutic molecule with irradiation energy to produce a liberated therapeutic molecule, where the biological activity of the liberated therapeutic molecule is greater than the biological activity of the nanomaterial composition.

The present disclosure further provides nanoparticle-based methods of providing a treatment to a living system involving: a) administering to the living system a nanomaterial composition including a nanoparticle linked, via a linker, to a drug base scaffold attached to a therapeutic molecule, and b) irradiating the living system with irradiation energy sufficient to cleave the link between the nanoparticle and the therapeutic molecule to produce a liberated therapeutic molecule, where the biological activity of the liberated therapeutic molecule is greater than the biological activity of the nanomaterial composition.

Delivery of Nanomaterial Compositions

The methods of the present disclosure involve providing a nanomaterial composition to a target. The target may be, for example, a target cell such as a cancer cell. The target may also be, for example, a living system such as a living cell, tissue, organ, or organism. One of skill in the art will readily recognize additional types of targets for the nanomaterial compositions of the present disclosure.

The nanomaterial compositions may be delivered to the target by various means known in the art. The nanomaterial compositions may be, for example, incubated with the target, they may be injected into the target, and they may be ingested by the target. One of skill in the art will readily recognize that various methods of delivering nanomaterial compositions of the present disclosure to a target exist and may be used in the methods described herein.

The nanomaterial compositions of the present disclosure may exhibit activated delivery to a target location. The use of irradiation energy, such as X-rays, facilitates the activation of the delivered inactive molecule in a nanomaterial composition, such as a nanoparticle drug carrier, at a target location.

Irradiation Energy

The nanomaterial compositions of the present disclosure may be delivered to a target so that a therapeutic molecule in the nanomaterial composition may become liberated by the cleaving of the linker between the nanoparticle and the therapeutic molecule. The methods of the present disclosure involve providing irradiation energy to cleave the link between the nanoparticle and the therapeutic molecule. The cleaving of this link may be caused by electrons or reactive oxygen species generated as a result of irradiation energy making contact with the nanoparticle. This contact results in the generation of reactive electrons or reactive electron-containing species. These electrons or reactive oxygen species act to cleave the chemical bonds in the linker molecule, thus severing the linkage between the nanoparticle and the therapeutic molecule. Therapeutic molecules that are no longer connected to the nanoparticle via the linker may be referred to as liberated therapeutic molecules. Various types of irradiation energy and methods of delivering such irradiation energy are discussed herein.

The irradiation energy used to cleave the link between the nanoparticle and the therapeutic molecule may be X-rays. Other ionizing radiation may be used such as, for example, high energy electrons, MeV gamma rays, and X-rays from various sources including accelerator-based laser produced monochromatic X-rays. The source of X-rays may also be a commercial microfocus X-ray source.

Various doses of irradiation energy may be used to cleave the link between the nanoparticle and the therapeutic molecule in a nanomaterial composition. The irradiation energy dose may be at least about 0.1 Gy, at least about 0.5 Gy, at least about 1 Gy, at least about 2 Gy, at least about 3 Gy, at least about 4 Gy, at least about 5 Gy, at least about 6 Gy, at least about 7 Gy, at least about 8 Gy, at least about 9 Gy, at least about 10 Gy, at least about 11 Gy, at least about 12 Gy, at least about 13 Gy, at least about 14 Gy, at least about 15 Gy, at least about 16 Gy, at least about 17 Gy, at least about 18 Gy, at least about 19 Gy, at least about 20 Gy, at least about 21 Gy, at least about 22 Gy, at least about 23 Gy, at least about 24 Gy, or at least about 25 Gy. The irradiation energy dose may be, for example, less than about 1 Gy or less than about 0.1 Gy. The irradiation energy dose may be, for example, about 25 Gy. The irradiation energy dose may be, for example, greater than about 25 Gy.

Enhancing Liberation of the Therapeutic Molecule

Cleaving the link between the nanoparticle and the therapeutic molecule produces a liberated therapeutic molecule. The liberated therapeutic molecule has greater biological activity than the biological activity of a nanomaterial composition. It is desirable to maximize the liberation of the therapeutic molecule from a nanoparticle so that the liberated therapeutic molecule can exert its biological activity in a target, such as a target cell, and thus provide treatment.

A variety of means may be used to enhance the liberation of the therapeutic molecule from the nanoparticle. For example, nanoparticles other than those within the nanomaterial compositions may be aggregated to the surface of the nanomaterial compositions to enhance the irradiation energy absorption and subsequent generation of reactive oxygen species or electrons that may directly cleave the bond of molecular linkers. The use of nanoparticles with a magnetic core may be used to aggregate in situ in the target cell to enhance absorption of irradiation energy by the nanoparticle or to enhance the release of the therapeutic molecule from the nanoparticle. These enhancement methods may be combined with geometry enhancement using bio-inspired or in situ assembly of irradiation energy absorbing nanoparticles around the nanomaterial compositions to enhance the generation of irradiation energy-induced electrons and/or reactive oxygen species. Chemical enhancement methods may also be used to cleave the chemical bonds in the linker molecules. For example, reactive oxygen species may react with the surface of nanoparticles in the nanomaterial compositions to catalyze the cleaving of the chemical bond in the linker, especially near the surface of the nanoparticle to which the linkers are attached.

Specially configured X-rays may be used to enhance the efficacy of X-ray triggered release of the therapeutic molecule. For example, a gamma knife operated at a low dose regime may be used to irradiate the site of linker cleavage, such as a target cell. The target cell should preferably be detected prior to training X-ray beams to the site. The increased absorption of X-ray irradiation energy by nanoparticles at the target site by specific targeting may help increase the efficiency of therapeutic molecule release from the nanoparticle. The irradiation dose enhancement through the gamma knife effect may also be used to trigger the release at a dose much lower than a normal treatment dose.

The biological activity of liberated therapeutic molecules of the present disclosure is greater than the biological activity of the nanomaterial compositions. The nanomaterial composition may be considered to carry a prodrug version of the therapeutic molecule. The biological activity of the liberated therapeutic molecule may be, for example, anticancer activity or other cytotoxic activity. The liberated therapeutic molecule may reduce target cell proliferation by about 3% per Gy of X-ray radiation. The liberated therapeutic molecule may reduce target cell proliferation by more than 3% per Gy of X-ray radiation.

EXAMPLES

To better facilitate an understanding of the embodiments of the disclosure, the following examples are presented. The following examples are merely illustrative and are not meant to limit any embodiments of the present disclosure in any way.

Example 1: X-ray Triggered Release of Doxorubicin from Nanoparticle Drug Carriers for Cancer Therapy The following example demonstrates that a specially designed nanoparticle drug carrier (NDC) can provide triggered release of drug molecules in cancer cells under X-ray irradiation. This is the first demonstration of increased cytotoxicity from X-ray triggered release of chemotherapeutic drugs from NDCs in cells.

Materials and Methods
Flow Cytometry.
MCF-7 Cells were plated at a density of 400,000 cells/well in a 24 well cell culture plate. After 24 hours, cells were incubated for 12 hours with 0, 100 nM, 400 nM, 600 nM DOX, as well as 1 nM DNA-AuNP and 1 nM DOX-DNA-AuNP. Cells were washed 3 times with PBS, and designated DOX-DNA-AuNP samples were then irradiated with 10 Gy of X-ray radiation. The cells were then trypsinized and placed in round bottom test tubes. Flow cytometry was used to measure the fluorescence from at least 10,000 cells using an upgraded BD FACScan—five-color Cytek (Cytek Development, Fremont, Calif.). Data was analyzed using FlowJo v7.6.5, Ashland, Oreg.

Construction of Gold Nanoparticles (AuNPs).
Gold chloride ($HAuCl_4$) and sodium citrate were purchased from Sigma-Aldrich. Dimethylsulfoxide (DMSO) was obtained from Fluka. Modified oligonucleotides were purchased from Sigma-Genosys and IDT. Water was purified with a Millipore Biocel system (18.2 Me). X-ray irradiation was performed in an HP Faxitron Model 4385SA (3.3 Gy/min at 100 kVp). Fluorescence measurements were made, using a Jobin-Yvon Horiba Fluoromax-P fluorometer. Transmission Electron Microscopy (TEM) was performed using a JEOL 1230 at 120 KeV.

DNA-Coated Gold Nanoparticles (DNA-AuNP).
16 nm gold nanoparticles (AuNPs) were synthesized using a modified method from Turkevich (Turkevich et al., 1951). Briefly, 5.25 mL of a 1% (w/v) sodium citrate solution were injected to a solution of 15 mg $HAuCl_4$ in 150 mL $H_2O$ which had been brought to reflux, under stirring. The solution was stirred at reflux for an additional 15 minutes, and then allowed to cool to room temperature. The AuNPs were functionalized with Carboxyfluorescein (6-FAM) labeled thiol-DNA (6-FAM-5'-(TTAGGG)$_n$-3'-C3-SH) of various lengths (n=1, 2, 4) using a modified method from Dhar (Dhar et al., 2009). Briefly, 50 µL of 100 µM 6-FAM-DNA was added to 5 mL of 1 nM AuNPs and allowed to incubate for 10 minutes before the addition of 50 µL of a 1% (w/v) Tween 20 solution. After an additional 10 minutes, 50 µL of 1 M phosphate buffer (PB), and 5 mL of 2M NaCl (in 10 mM PB) were added and the solution was allowed to incubate overnight. The free DNA was removed from solution by centrifuging five times (13,000 rpm, 15 min) and redispersed in PBS (100 mM NaCl, 10 mM PB, pH=7.4). The average size of AuNPs is 15.9±1.2 nm.

Doxorubicin Conjugation to DNA-AuNPs.
Using a method developed by Wang (Wang et al., 2011), all solutions were prepared in anhydrous dimethylformamide (DMF). To 431 µL of 2 mM doxorubicin purchased from LC Laboratories, 37.4 µL of 0.0717 M triethylamine (TEA) and 20 µL of 0.0472 M succinic anhydride were added and reacted for 3 hours. Solutions of 1-Ethyl-3-[3-dimethylaminopropyl]carbodiimide hydrochloride (EDC) and N-hydroxysuccinimide (NHS) were prepared by dissolving 33.0 mg of EDC and 19.8 mg NHS in 1 mL volumes of DMF with vortexing and sonication. To the succinic-doxorubicin solution, 20 µL each of the EDC and NHS solutions were added. All subsequent reactions were performed in PBS (100 mM NaCl, 10 mM PB, pH=7.4). To 2.50 mL of amine-terminated DNA-AuNPs ($NH_2$—$C_6$-5'-TTAGGGTTAGGG-3'-$C_3$—SH—AuNP), 75 µL of 2 mM polyethylene glycol (mPEG-SH, MW 2000) were added. The solution was briefly vortexed to mix, and allowed to react for 10 minutes before 132 µL of the activated doxorubicin was added. The solution reacted overnight, and the DOX-DNA-AuNPs were then washed five times by centrifuging (13,000 rpm, 15 min) with PBS (100 mM NaCl, 10 mM PB, pH=7.4). The resuspended solution was subsequently cleaned by centrifuging twice in a 10K Millipore filter (7,000 rpm, 10 min) and the solution in the filter was recovered.

X-ray Radiation with DMSO.
X-ray radiation studies were performed, using DMSO as a hydroxyl radical scavenger at concentrations from 0-100 mM. In a 24-well plate, 400 µL of purified 6-FAM-DNA-AuNPs were mixed with 400 µL of 2×DMSO solution, or PBS and the samples were irradiated with X-rays. After radiation, the AuNPs were removed from solution by centrifugation (13,000 rpm, 15 min) and supernatant fluorescence was measured (Excitation at 490 nm and Emission at 514 nm). Non-radiated controls were identically prepared and measured.

X-ray Radiation with Quenching DNA.

The 6-FAM-DNA-SH compound has one 6-FAM attached to the end of a thiolated DNA strand, and is available commercially. The average size of AuNPs was measured, using TEM counting over 200 nanoparticles (15.9±1.2 nm). 6-FAM has a high fluorescence yield (>80%) and high quenching when attached to AuNPs. The cleavage via X-ray irradiation was studied with optical fluorescence spectroscopy.

Black Hole Quencher®-1 DNA, coupled to 6-FAM, was purchased from IDT (6-FAM-5'-TTAGGGTTAGGG-3'-BHQ-1®). It was irradiated with DMSO at concentrations from 0-100 mM in 24 well plates, and the fluorescence from cleaved DNA was measured. The fluorescence signal and, hence cleavage was found to be approximately linearly dependent of the length of DNA and the dose of X-rays. X-ray radiated and cleaved 6-FAM molecules were incubated with MCF-7 cells for 4 hours.

Optical Fluorescence Microscopy.

Optical fluorescence microscopy (Leica DFC310 FX) was used to image the cells. Optical microscopy was also used to verify that 6-FAM molecules were cleaved with X-rays. Due to the cleavage of DNA by X-ray radiation, 6-FAM was cleaved off the surface of AuNPs and they caused cells to be fluorescent.

Clonogenic Assay.

MCF-7 cells were plated at a rate of 50,000 cells/ml in a 24-well cell culture plate. They were then incubated with DOX, DOX-DNA, and DOX-DNA-AuNPs for 12 hours, and then irritated with 0, 2, 5, and 10 Gy X-rays. The cells were then counted, using a hemocytometer, and replated in a 6 well plate at 1000 cell per well for the 0 and 2 Gy dose; 3000 cells for the 5 Gy; and 9000 for the 10 Gy. The plates were incubated for 14 days, and then fixed with gluteraldhyde and stained with crystal violet. The colonies with 50 or more cells were then counted.

Results

Doxorubicin (DOX), gold nanoparticles (AuNPs), DNA-coated AuNPs (DNA-AuNP), and DOX conjugated to DNA-AuNPs (DOX-DNA-AuNPs) were synthesized. These materials were incubated with MCF-7 breast cancer cells. Flow cytometry was used to measure the uptake of these chemicals. X-ray irradiation was performed, and toxicity was measured with clonogenic assay. In addition, Black Hole Quencher®-1 DNA coupled to 6-Carboxyfluorescein (6-FAM) was used to model the release of DOX from DOX-DNA-AuNPs. Fluorescence spectroscopy was used to characterize X-ray radiation triggered release of 6-FAM. See Materials and Methods.

DOX, DNA-AuNPs, and DOX-DNA-AuNPs were incubated with MCF-7 cells for 12 hours. Based on the fluorometry-calibrated flow cytometry data, DOX uptake was of the order of 24 million per cell, as shown in Table 1-1. The number of AuNPs per cell was 14 million, measured with ICP-MS after incubation with 1 nM DNA-AuNPs or DOX-DNA-AuNPs for 12 hours. Because fluorescence of DOX on AuNPs was largely quenched, DOX-DNA was removed from the gold surface using dithiolthreitol (DTT), and the purified DOX-DNA samples were measured with fluorometry. The results showed that there were approximately 25 billion DOX per cell through the uptake of DOX-DNA-AuNPs, with an average of 1785 DOX per AuNP.

TABLE 1-1

DOX Uptake Results

|  | DOX | DNA-AuNP | DOX from DOX-DNA-AuNPs | DOX Released after 10 Gy |
|---|---|---|---|---|
| Per Cell | 24 ± 2.5 (100 nM) | 14 ± 1.3 (1 nM) | 25000 ± 2000 (1 nM) | 21 ± 1.3 (1 nM) |

(Average number (in million) per cell). Incubation concentrations are shown in parentheses.

Figure 1:
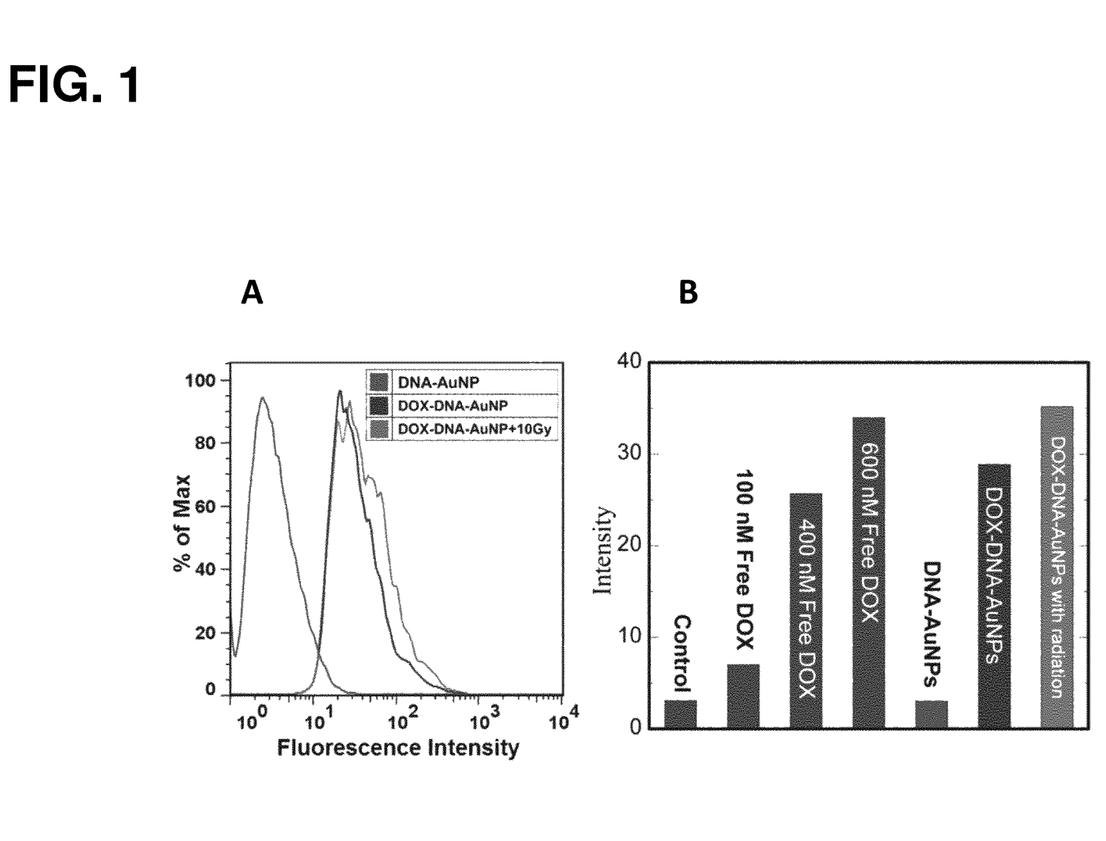
FIG. 1A illustrates flow cytometry data and the uptake and release data after sample irradiation with 10 Gy.
FIG. 1B illustrates the median signals for 3 samples incubated with free DOX and three samples with DNA-AuNPs.

FIG. 1A shows the flow cytometry data and median values of the flow cytometry measurements are shown in FIG. 1B. There is a high level of DOX fluorescence, corresponding to 90 million free DOX per cell, after incubation with DOX-AND-AuNPs but before X-ray irradiation. If this signal were from free DOX, toxicity would be 4-5 times greater (see below), which was not observed. Instead, this pre-irradiation fluorescence signal came from both naturally released DOX in the cell and unquenched DOX-DNA-AuNPs. Because the amount of DOX naturally cleaved off the surface of AuNPs was only a small fraction (14.5 million, see below) of that on NDC (25 billion) per cell, the quenching efficiency of DOX attached through DNA strands to AuNPs was estimated to be 99.7%.

Figure 2:
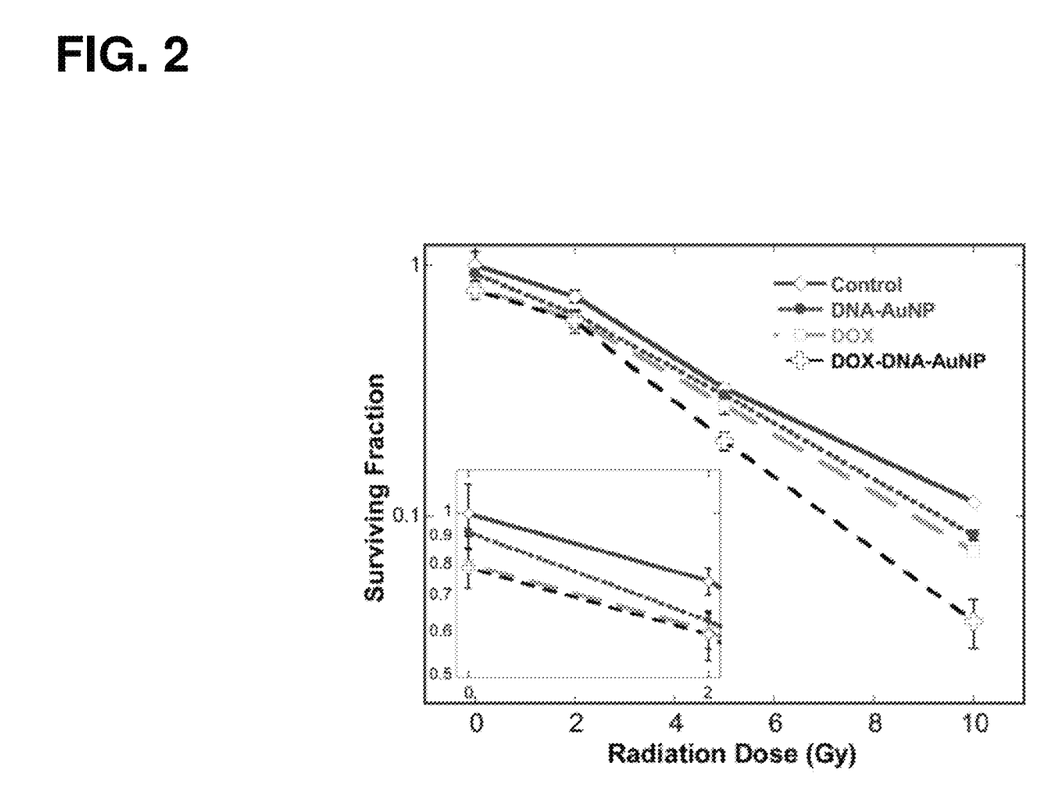
FIG. 2 illustrates cell survivability before and after exposure to X-ray irradiation. The cells were incubated with several samples, including a control, DNA-AuNPs, DOX, and DOX-DNA-AuNPs NDC. DOX-DNA-AuNPs are the most lethal among these samples. Inset shows the data at zero and 2 Gy of radiation.

Clonogenic assay was used to determine the effects of radiation, drugs, and nanomaterials (Franken et al., 2006). The results of clonogenic assays are shown in FIG. 2. The inset of FIG. 2 shows the data at zero and 2 Gy of radiation. DOX alone caused about 20% toxicity (or 80% survivability) to MCF-7 cells, which was caused by 24 million free DOX in the cell (see Table 1-1).

Upon irradiation, DOX-DNA-AuNPs NDC became more toxic than the sum of radiation and NDC, as shown in FIG. 2 and Table 1-2. NDC became more toxic with higher X-ray dosage, going from −1%±15% at 2 Gy to +19%±13% at 5 Gy and +33%±21% at 10 Gy. Without wishing to be bound by theory, it is believed that given the amount of AuNPs in the cell (~30 wt %), the observed small amount of enhanced toxicity suggests that these nanoparticles stayed in the cytoplasm because this amount of AuNPs in the cell would cause significant damage if only X-ray absorption enhancement is considered (Carter et al., 2012; Lechtman et al., 2011). For treatment of breast cancer patients using radiotherapy of a standard 50 Gy total dose in 5-10 fractions (Fisher et al., 1985), the current NDC would generate a significantly increased toxicity of 165% to the tumor. The NDC designed here may be used in the currently popular hypofractionated radiotherapy in which multiple fractions of 5-12 Gy per fraction are administrated (Kwon et al., 2009; Martucci et al., 2011; Janssen et al., 2012; Senthi et al., 2010).

TABLE 1-2

Cytotoxicity Analysis

| Samples | 0 Gy | 2 Gy | 5 Gy | 10 Gy |
|---|---|---|---|---|
| Control | 1.00 ± .14 | 0.75 ± .04 | 0.32 ± .01 | 0.11 ± .001 |
| DOX | 0.81 ± .01 | 0.61 ± .05 | 0.28 ± .02 | 0.07 ± .002 |
| DNA-AuNPs | 0.92 ± .02 | 0.64 ± .02 | 0.30 ± .03 | 0.08 ± .004 |
| DDA | 0.80 ± .07 | 0.60 ± .06 | 0.20 ± .02 | 0.04 ± .008 |
| Enhancement | 0% ± 12% | −1% ± 15% | 19% ± 13% | 33% ± 21% |

Measured cell survivability (numerical values) and enhancements (DDA stands for DOX-DNA-AuNPs)

6-Carboxyfluorescein (6-FAM) was used to quantitatively study the release of DOX from AuNPs via DNA cleavage under X-ray irradiation. The fluorescence signal and hence the cleavage was found to be approximately linearly dependent on the length of DNA and the dose of X-rays. These results support that the DNA strands were cleaved and DOX molecules were removed from the surface of AuNPs under X-ray irradiation. When polyethylene glycol (PEG) was used to replace DNA, the amount of cleavage for PEG ligands was reduced to less than 10% of the original signal. This result suggests that the release of 6-FAM was caused by cleavage of DNA molecules.

DTT was used to remove the thiolated DNA strands, and the fluorescence from 6-FAM was used to estimate the number of DNA strands per AuNPs, which were found to be 213. Using the number of DOX per AuNP obtained earlier, it was believed that all possible conjugating sites on DNA were occupied by DOX, with approximately 9 DOX molecules per DNA strand.

Figure 3:
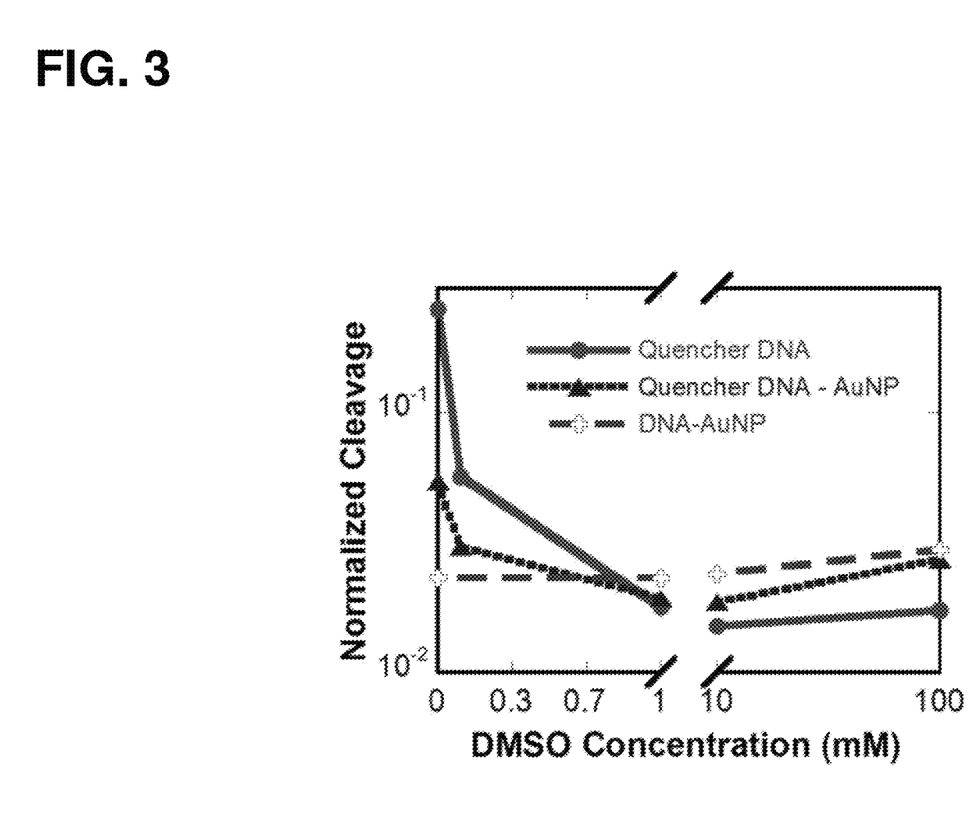
FIG. 3 illustrates cleavage of 6-FAM in three samples. The solid line shows the signal from Q-DNA-6-FAM as a function of DMSO. 25% of DNA strands between Q and 6-FAM are cleaved after 100 Gy of X-ray radiation. When AuNPs are added to Q-DNA-6-FAM, only 4% of 6-FAM are cleaved (dotted line). When 6-FAM are anchored on the surface of AuNPs, radiation cleaved 2.5% of 6-FAM (dashed line), and the same amount of cleavage remained at up to 100 mM DMSO.

To further confirm that the detected fluorescence signal after X-ray irradiation was actually from the cleaved 6-FAM-DNA molecules, a quencher-DNA-6-FAM (Q-DNA-6-FAM) compound (Blackhole Quencher®) was tested. After 100-Gy X-ray irradiation, 25% of Q-DNA-6-FAM cleavage occurred and the sample became fluorescent again, as shown in FIG. 3 (red solid line). Adding dimethyl sulfoxide (DMSO), a hydroxyl radical (.OH) scavenger, significantly reduced the fluorescence. These results suggest that X-ray generated .OH is the main cause for cleavage of DNA strands. In the presence of AuNPs (mixture, no covalent conjugation), the amount of fluorescence was reduced to only ~4% after 100-Gy X-ray irradiation (dotted line in FIG. 3 at zero DMSO). The amount of DNA cleavage in 6-FAM-DNA-AuNPs was 2.5% (FIG. 3, solid vs. dashed lines at zero DMSO). This demonstrates that AuNPs are highly scavenging towards radicals, behaving similarly to that of DMSO. Without wishing to be bound by theory, it is believed that this is observed because the gold surface is an effective reactive oxygen species (ROS) scavenger (Carter et al., 2012; Cheng et al., 2012).

As described above, each DNA carries 9 DOX. When a cleavage occurs, the DNA may be broken anywhere along the strand, releasing between 1 and 9 DOX. On average, 4.5 DOX molecules are released per cleavage.

DOX on NDC were much less toxic without X-ray activation. 25 billion DOX on AuNPs with ~14.5 million free DOX via natural cleavage caused the same toxicity as 24 million free DOX in the cell. Without wishing to be bound by theory, it is believed that this result agrees with the accepted mechanisms of DOX toxicity in which they diffuse into nuclei and intercalate with nuclear DNA (Formari et al., 1994). When the DOX are bound to large AuNPs, the diffusion efficiency and the ability to enter the nuclei are significantly reduced. Without wishing to be bound by theory, it is believed that the toxicity of NDC without irradiation observed here comes from a small amount of free DOX or the equivalent removed from NDC by natural enzymatic cleavage or ligand exchange reactions in the cell (Han et al., 2006).

Conclusions

NDCs were synthesized and uptake and radiation toxicity were measured using MCF-7 breast cancer cells. The results presented in this Example demonstrate that the extra toxicity shown in clonogenic assay was caused by additional DOX released from the surface of AuNPs in the cell triggered by X-ray irradiation.

Example 2: Construction of X-Ray Activated Nanoparticle Drug Carriers (NDC) and Delivery to Cancer Cells This example demonstrates the construction of an exemplary X-ray activated nanoparticle drug carrier (NDC) that can be activated to release a lethal dose ($LD_{50}$) of drugs into breast cancer cells (MCF-7 and SK-BR-3) after exposure to 0.1-1 Gy X-rays between 82 and 90 keV, an energy region selected for optimal X-ray absorption by gold (Au). The NDC contains three components: i) X-ray absorbing nanoparticles; ii) radical cleavable linkers; and iii) drug base scaffolds, all of which are designed for 1) uptake by a cell; 2) stability in the cell; 3) targeting the breast cancer cells; and 4) drug release by X-rays.

Construction of NDCs.

An NDC is constructed that contains three features as mentioned above. An exemplary embodiment of an NDC is provided in FIG. 4. The first feature is the gold nanoparticle (AuNP) that functions as an X-ray absorber. The electrons emitted from the nanoparticles after X-ray absorption produce reactive oxygen species (ROS) such as OH radicals (.OH) in a water layer (~4 nm thick) immediately surrounding the silica-coated AuNPs. The second feature is the linker L', linking the drug clusters to the $SiO_2$ surface. L' can be easily cleaved by reacting with .OH generated within the water layer around AuNPs, without interference from other chemicals. The length of L' defines the thickness of the water layer. The third feature is the clustered drugs (nDL) on a drug base scaffold L. Multiple drug molecules (nD) are conjugated to each of the short polymers L such as DNA or hyaluronic acid (HA), forming clusters. The bulkiness of nDL defines the outer boundary of the water layer. Targeting moieties (T) linked to the surface of AuNPs complete the design of NDC. PEG ligands may be added to the surface of AuNPs@$SiO_2$ to increase its solubility.

The NDCs have a size (50 nm) that allows for surface energy deposition. The NDCs also have a silica coating (5 nm thick) to promote .OH radical attack of the linker L'. Linker L' is composed of a 12-mer single strand DNA (ssDNA) molecule. The drug base scaffold (DBS) L is also composed of a 12-mer single strand DNA (ssDNA) molecule. The therapeutic drug used is doxorubicin (DOX). DOX is attached to the drug base scaffold so that radicals can directly attack the linker (L') DNA strand to cleave the DNA strand, facilitating the release of the drug clusters from the AuNPs.

Uptake of NDC and Targeting HER2-Overexpressing Breast Cancer Cells.

NDCs are incubated with MCF-7 (HER2 negative) and SK-BR-3 (HER2 positive) cells, and the uptake of NDCs is determined by ICP-MS measurements after different incubation times (1 to 12 hours). When targeting peptides are attached to the surface of NDCs, the NDCs are incubated with HER2 overexpressing SK-BR-3 cells and control MCF-7 cells to confirm accurate cellular targeting by the NDC.

X-ray Triggered Release of Drugs and Cellular Toxicity.

Clonogenic assays are used to evaluate cellular toxicity. NDC are incubated with the cells for more than 1 hour. For X-ray triggered release, two X-ray doses are evaluated to compare efficacy: a dose of 1 Gy and a dose of 0.1 Gy or less. Control experiments using X-rays alone are performed. The drug release ability of NDC in cells is measured and quantified.

In Vivo Analysis of NDC Efficacy in Treating Cancer-Bearing Mice.

Breast cancer tumor cells (MCF-7) are injected into the right flank of 4 nude mice. Tumors are allowed to grow for two weeks until the tumor size reaches the order of 2-4 mm. Three different concentrations of NDC are subcutaneously injected into 3 of the 4 mice. The fourth mouse is used as a control for X-ray irradiation only. These 4 mice are imaged (<1 sec) 4 hours after the NDC injection with a microCT (Inveon SPECT/CT, X-ray energy set at 80 keV). When NDC are confirmed to reach the tumor, the animals are treated (~100 sec, corresponding to 1 Gy) with the same microCT. Two other nude mice are used to test the toxicity of the NDC with and without the drug, and they are imaged (1 sec exposure) with the microCT. After CT imaging and treatment, mice are anesthetized using intraperitoneal injection of ketamine/xylazine. Tumors, organs, and tissues are excised and studied.

Subsequently, 9 groups of mice, 5 mice in each group, are employed to ensure statistical relevant P values. An X-ray dose of 0.1 Gy (10 sec) is used to determine the efficacy of NDCs. SK-BR-3 cells and MCF-7 cell-infected mice are used.

REFERENCES

1. A. Dimarco, M. Gaetani and Scarpina. B, *Cancer Chemotherapy Reports Part* 1, 1969, 53, 33-37.
2. D. D. Vonhoff, M. W. Layard, P. Basa, H. L. Davis, A. L. Vonhoff, M. Rozencweig and F. M. Muggia, *Annals of Internal Medicine*, 1979, 91, 710-717.
3. M. Rooseboom, J. N. M. Commandeur and N. P. E. Vermeulen, *Pharmacological Reviews*, 2004, 56, 53-102.
4. A. Gabizon, R. Catane, B. Uziely, B. Kaufman, T. Safra, R. Cohen, F. Martin, A. Huang and Y. Barenholz, *Cancer Research*, 1994, 54, 987-992.
5. H. C. Arora, M. P. Jensen, Y. Yuan, A. G. Wu, S. Vogt, T. Paunesku and G. E. Woloschak, *Cancer Research*, 2012, 72, 769-778.
6. G. T. Qin, Z. Li, R. M. Xia, F. Li, B. E. O'Neill, J. T. Goodwin, H. A. Khant, W. Chiu and K. C. Li, *Nanotechnology*, 2011, 22, 155605.
7. S. Dhar, W. L. Daniel, D. A. Giljohann, C. A. Mirkin and S. J. Lippard, *Journal of the American Chemical Society*, 2009, 131, 14652-14653.
8. A. Schroeder, J. Kost and Y. Barenholz, *Chemistry and Physics of Lipids*, 2009, 162, 1-16.
9. J. L. West, A. M. Gobin, M. H. Lee, N. J. Halas, W. D. James and R. A. Drezek, *Nano Letters*, 2007, 7, 1929-1934.
10. D. M. Liu, S. H. Hu, Y. Y. Chen, T. C. Liu, T. H. Tung and S. Y. Chen, *Chemical Communications*, 2011, 47, 1776-1778.
11. L. V. Wang, W. Y. Li, X. Cai, C. H. Kim, G. R. Sun, Y. Zhang, R. Deng, M. X. Yang, J. Y. Chen, S. Achilefu and Y. N. Xia, *Nanoscale*, 2011, 3, 1724-1730.
12. D. F. O'Brien, K. A. McGovern, B. Bondurant and R. Sutherland, Varian Medical Systems Technologies, Inc.; Arizona Board of Regents on Behalf of the University of Arizona, USA, 2001.
13. T. M. Nguyen, S.-K. Kim, J. Capala and S. B. Lee, in *The 238th ACS National Meeting*, Washington, D.C., 2009.
14. E. Foley, J. Carter, F. Shan and T. Guo, *Chem. Commun.*, 2005, 3192-3194.
15. J. D. Carter, N. N. Cheng, Y. Q. Qu, G. D. Suarez and T. Guo, *J. Phys. Chem. B*, 2007, 111, 11622-11625.
16. J. P. Scaffidi, M. K. Gregas, B. Lauly, Y. Zhang and T. Vo-Dinh, *Acs Nano*, 2011, 5, 4679-4687.
17. K. Tanabe, J. Ishizaki, Y. Ando, T. Ito and S. I. Nishimoto, *Bioorganic & Medicinal Chemistry Letters*, 2012, 22, 1682-1685.
18. G. O. Ahn, D. C. Ware, W. A. Denny and W. R. Wilson, *Radiation Research*, 2004, 162, 315-325.
19. M. Bontenbal, A. M. Sieuwerts, H. A. Peters, W. L. J. van Putten, J. A. Foekens and J. G. M. Klijn, *Breast Cancer Research and Treatment*, 1998, 51, 139-148.
20. D. A. Giljohann, D. S. Seferos, P. C. Patel, J. E. Millstone, N. L. Rosi and C. A. Mirkin, *Nano Letters*, 2007, 7, 3818-3821.
21. N. A. P. Franken, H. M. Rodermond, J. Stap, J. Haveman and C. van Bree, *Nature Protocols*, 2006, 1, 2315-2319.
22. J. D. Carter, N. N. Cheng, Y. Q. Qu, G. D. Suarez and T. Guo, *J. Colloid Interf. Sci.*, 2012, 378, 70-76.
23. E. Lechtman, N. Chattopadhyay, Z. Cai, S. Mashouf, R. Reilly and J. P. Pignol, *Physics in Medicine and Biology*, 2011, 56, 4631-4647.
24. B. Fisher, M. Bauer, R. Margolese, R. Poisson, Y. Pilch, C. Redmond, E. Fisher, N. Wolmark, M. Deutsch, E. Montague, E. Saffer, L. Wickerham, H. Lerner, A. Glass, H. Shibata, P. Deckers, A. Ketcham, R. Oishi and I. Russell, *New England Journal of Medicine*, 1985, 312, 665-673.
25. A. K. Kwon, S. J. DiBiase, B. Wang, S. L. Hughes, B. Milcarek and Y. P. Zhu, *Cancer*, 2009, 115, 890-898.
26. F. Martucci, M. C. Valli, G. Pesce, A. Fozza, N. C. Azinwi and A. Richetti, *Strahlentherapie Und Onkologie*, 2011, 187, 529-529.
27. S. Janssen, N. J. Dickgreber, C. Koenig, M. Bremer, M. Werner, J. H. Karstens, T. Welte and A. Meyer, *Onkologie*, 2012, 35, 408-412.
28. F. J. L. S. Senthi, C. J A Haasbeek, B. J Slotman, S. Senan, *Oncology*, 2012, 13, 8.
29. N. N. Cheng, Z. Starkewolf, A. R. Davidson, A. Sharmah, C. Lee, J. Lien and T. Guo, *J. Am. Chem. Soc. Commun.*, 2012, 134, 1950-1953.
30. F. A. Formari, J. K. Randolph, J. C. Yalowich, M. K. Ritke and D. A. Gewirtz, *Molecular Pharmacology*, 1994, 45, 649-656.
31. G. Han, C. T. Martin and V. M. Rotello, *Chemical Biology & Drug Design*, 2006, 67, 78-82.
32. V. V. Moiseenko, R. N. Hamm, A. J. Waker and W. V. Prestwich, *Int. J. Rad. Bio.*, 1998, 74, 533-550.
33. Turkevich, J.; Stevenson, P. C.; Hillier, J., *Discussions of the Faraday Society* 1951, (11), 55.
34. Dhar, S.; Daniel, W. L.; Giljohann, D. A.; Mirkin, C. A.; Lippard, S. J., *Journal of the American Chemical Society* 2009, 131, (41), 14652.
35. Wang, F.; Wang, Y. C.; Dou, S.; Xiong, M. H.; Sun, T. M.; Wang, J., *Acs Nano* 2011, 5, (5), 3679-3692.

What is claimed is:

1. A nanoparticle-based method of providing a treatment to a target cell, the method comprising:
   (a) contacting the target cell with a nanomaterial composition, the nanomaterial composition comprising a nanoparticle linked, via a linker, to a therapeutic molecule, and
   (b) cleaving the link between the nanoparticle and the therapeutic molecule with irradiation energy of between about 0.1 Gy and 25 Gy to produce a liberated therapeutic molecule,
   wherein the biological activity of the liberated therapeutic molecule is greater than the biological activity of the nanomaterial composition.

2. The method of claim 1, wherein the nanomaterial composition further comprises a drug base scaffold wherein the drug base scaffold is attached to the linker and the drug base scaffold is attached to the therapeutic molecule.

3. The method of claim 2, wherein the drug base scaffold is a DNA molecule.

4. The method of claim 2, wherein the drug base scaffold comprises a scaffold molecule, and wherein the scaffold molecule is coupled with one to twelve therapeutic molecules.

5. The method of claim 4, wherein the cleavage releases more than one therapeutic molecule.

6. The method of claim 1, wherein the nanoparticle comprises a core comprising a metal.

7. The method of claim 6, wherein the metal is Au.

8. The method of claim 1, wherein the nanoparticle comprises a shell comprising silica.

9. The method of claim 8, wherein the shell has attached, at its surface, PEG ligands.

10. The method of claim 8, wherein the shell has attached, at its surface, targeting moieties.

11. The method of claim 8, wherein the nanomaterial composition further comprises a water layer immediately surrounding the shell comprising silica.

12. The method of claim 1, wherein the linker is a DNA molecule.

13. The method of claim 1, wherein the therapeutic molecule is doxorubicin.

14. The method of claim 1, wherein the irradiation energy is X-rays.

15. The method of claim 1, wherein the target cell is a cancer cell.

16. The method of claim 1, wherein the irradiation energy produces electrons or reactive oxygen species that participate in the link cleaving.

17. The method of claim 1, wherein the linker is directly coupled to the nanoparticle.

18. A nanoparticle-based method of providing a treatment to a living system, the method comprising:
 (a) administering to the living system a nanomaterial composition, the nanomaterial composition comprising a nanoparticle linked, via a linker, to a therapeutic molecule, and
 (b) irradiating the living system with irradiation energy of between about 0.1 Gy and 25 Gy sufficient to cleave the link between the nanoparticle and the therapeutic molecule to produce a liberated therapeutic molecule, wherein the biological activity of the liberated therapeutic molecule is greater than the biological activity of the nanomaterial composition.

19. The method of claim 18, wherein the nanomaterial composition further comprises a drug base scaffold wherein the drug base scaffold is attached to the linker and the drug base scaffold is attached to the therapeutic molecule.

20. The method of claim 19, wherein the drug base scaffold is a DNA molecule.

21. The method of claim 18, wherein the nanoparticle comprises a core comprising a metal.

22. The method of claim 21, wherein the metal is Au.

23. The method of claim 18, wherein the nanoparticle comprises a shell comprising silica.

24. The method of claim 23, wherein the shell has attached, at its surface, PEG ligands.

25. The method of claim 23, wherein the shell has attached, at its surface, targeting moieties.

26. The method of claim 18, wherein the linker is a DNA molecule.

27. The method of claim 18, wherein the therapeutic molecule is doxorubicin.

28. The method of claim 18, wherein the irradiation energy is X-rays.

29. The method of claim 18, wherein the living system comprises a cancer cell.

30. A nanoparticle-based method of providing a treatment to a target cell, the method comprising:
 delivering a nanomaterial composition to the target cell, the nanomaterial composition comprising a nanoparticle linked, via a linker, to a drug base scaffold to which one or more therapeutic molecules is coupled, and
 irradiating the nanomaterial composition with irradiation energy of between about 0.1 Gy and 25 Gy to cause one or more therapeutic molecules to decouple from the drug base scaffold.

31. The method of claim 30, wherein at least one of the drug base scaffold and the linker is a DNA molecule.

32. The method of claim 30, wherein at least one additional agent is coupled with the nanomaterial, wherein the additional agent comprises one or more of an antibody, a peptide, a protein, polyethylene glycol, or folic acid.

33. The method of claim 30, wherein the therapeutic molecule includes a molecule selected from the group consisting of Doxorubicin, Fluorouracil, Paclitaxel, Zevalin, Fredericamycin, C-1027, Leinamycin, a protein, a protease, a DNA nuclease, an enzyme, and small RNA.

* * * * *